VARIETY OF HOYA CARNOSA WITH TRICOLOR FOLIAGE

Filed Jan. 9, 1968 5 Sheets-Sheet 1

INVENTOR,
BARNELL L. COBIA by ROGER L. MARTIN
ATTORNEY

VARIETY OF HOYA CARNOSA WITH TRICOLOR FOLIAGE

Filed Jan. 9, 1968 5 Sheets-Sheet 3

INVENTOR,
BARNELL L. COBIA by ROGER L. MARTIN
ATTORNEY

VARIETY OF HOYA CARNOSA WITH TRICOLOR FOLIAGE
Filed Jan. 9, 1968 5 Sheets-Sheet 3
FIG. IV.
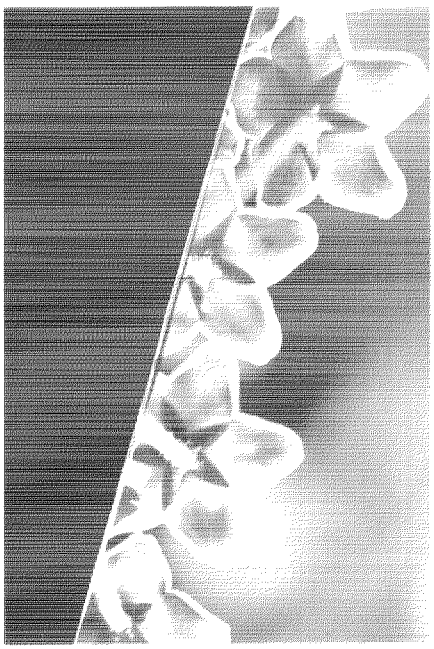
FIG. V.
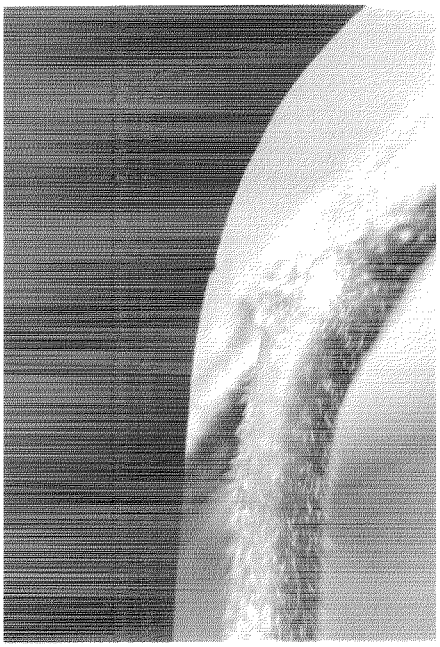
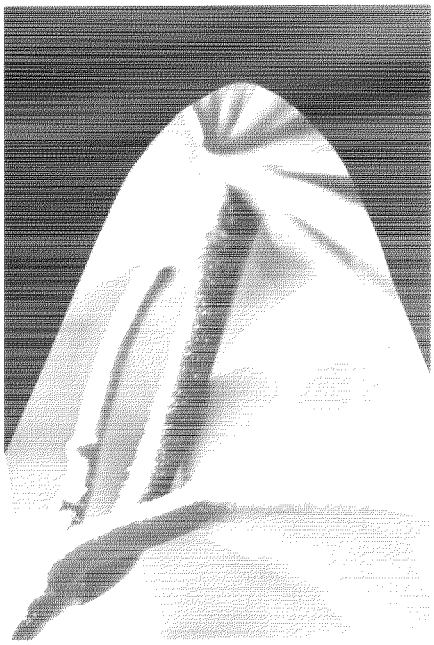
FIG. VI.
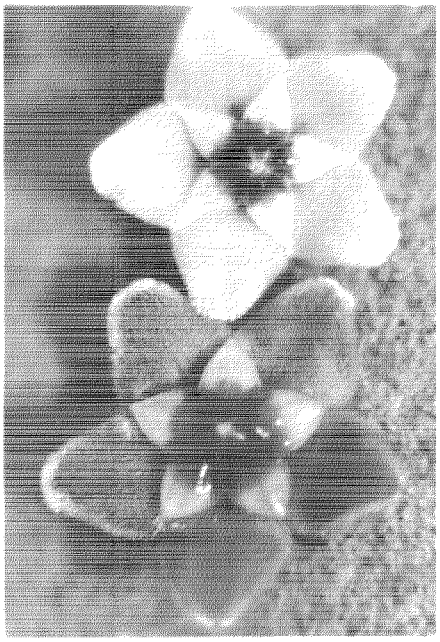
FIG. VII.
INVENTOR,
BARNELL L. COBIA
by ROGER L. MARTIN
ATTORNEY Dec. 9, 1969 B. L. COBIA Plant Pat. 2,950

VARIETY OF HOYA CARNOSA WITH TRICOLOR FOLIAGE

Filed Jan. 9, 1968 3 Sheets-Sheet 1

INVENTOR,
BARNELL L. COBIA by ROGER L. MARTIN
ATTORNEY

Dec. 9, 1969 B. L. COBIA Plant Pat. 2,950
VARIETY OF HOYA CARNOSA WITH TRICOLOR FOLIAGE
Filed Jan. 9, 1968 5 Sheets-Sheet 1
FIG. X
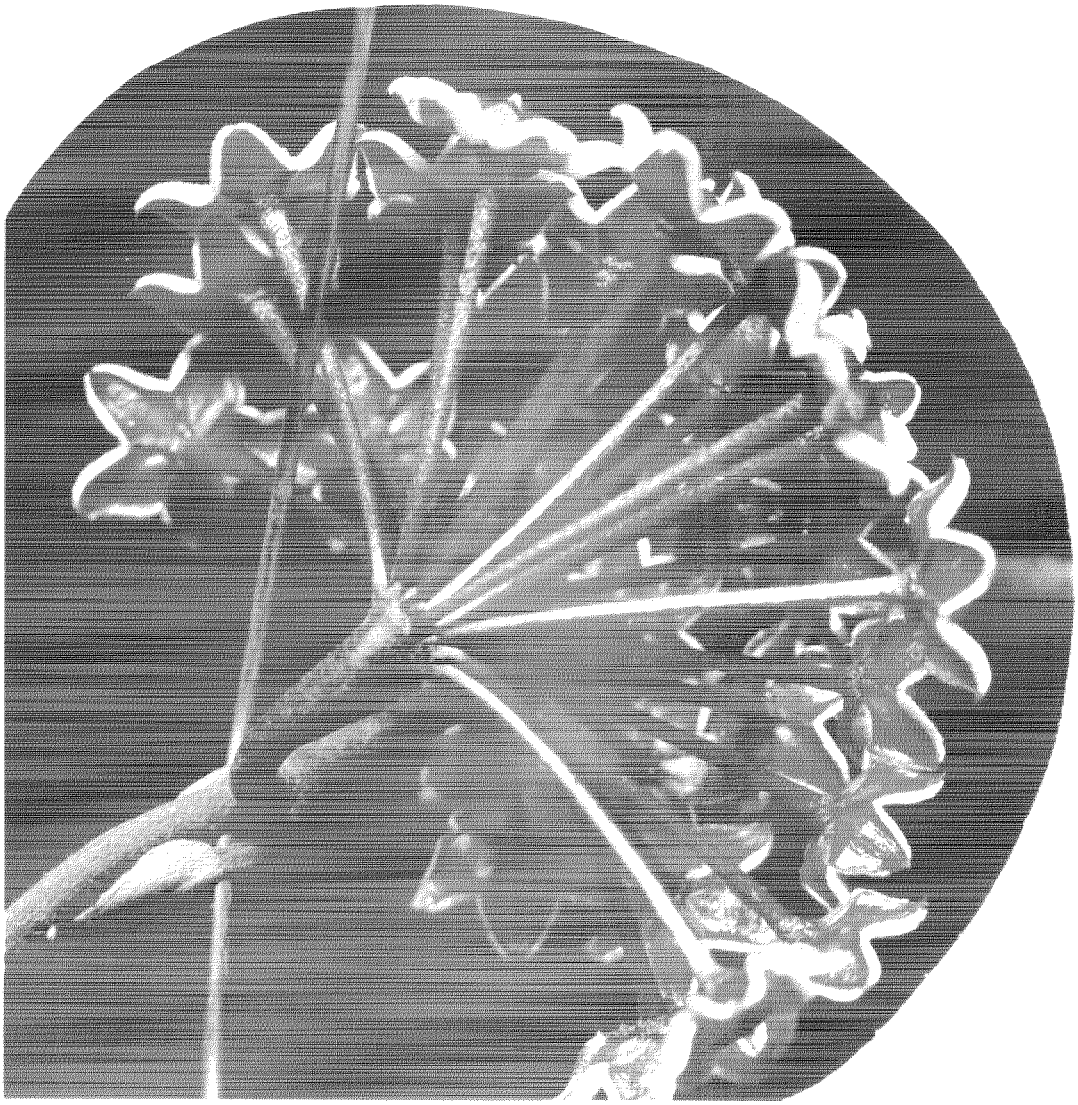
INVENTOR,
BARNELL L. COBIA
BY ROGER L. MARTIN
ATTORNEY United States Patent Office Plant Pat. 2,950
Patented Dec. 9, 1969

2,950
VARIETY OF *HOYA CARNOSA* WITH TRICOLOR FOLIAGE

Barnell L. Cobia, 135 Temple Grove Drive,
Winter Garden, Fla. 32787

Filed Jan. 9, 1968, Ser. No. 697,247
Int. Cl. A01h *5/02*
U.S. Cl. Plt.—88 1 Claim

ABSTRACT OF THE DISCLOSURE

The disclosure relates to a new and distinct plant variety of the milkweed (Asclepiadaceae) family. Plants of the new variety are related to and resemble plants of the *Hoya carnosa variegata* variety and also plants of an unnamed variety which are found in the foliage plant market and generally considered to be an improved strain of the *Hoya carnosa variegata* variety.

Figure 1:
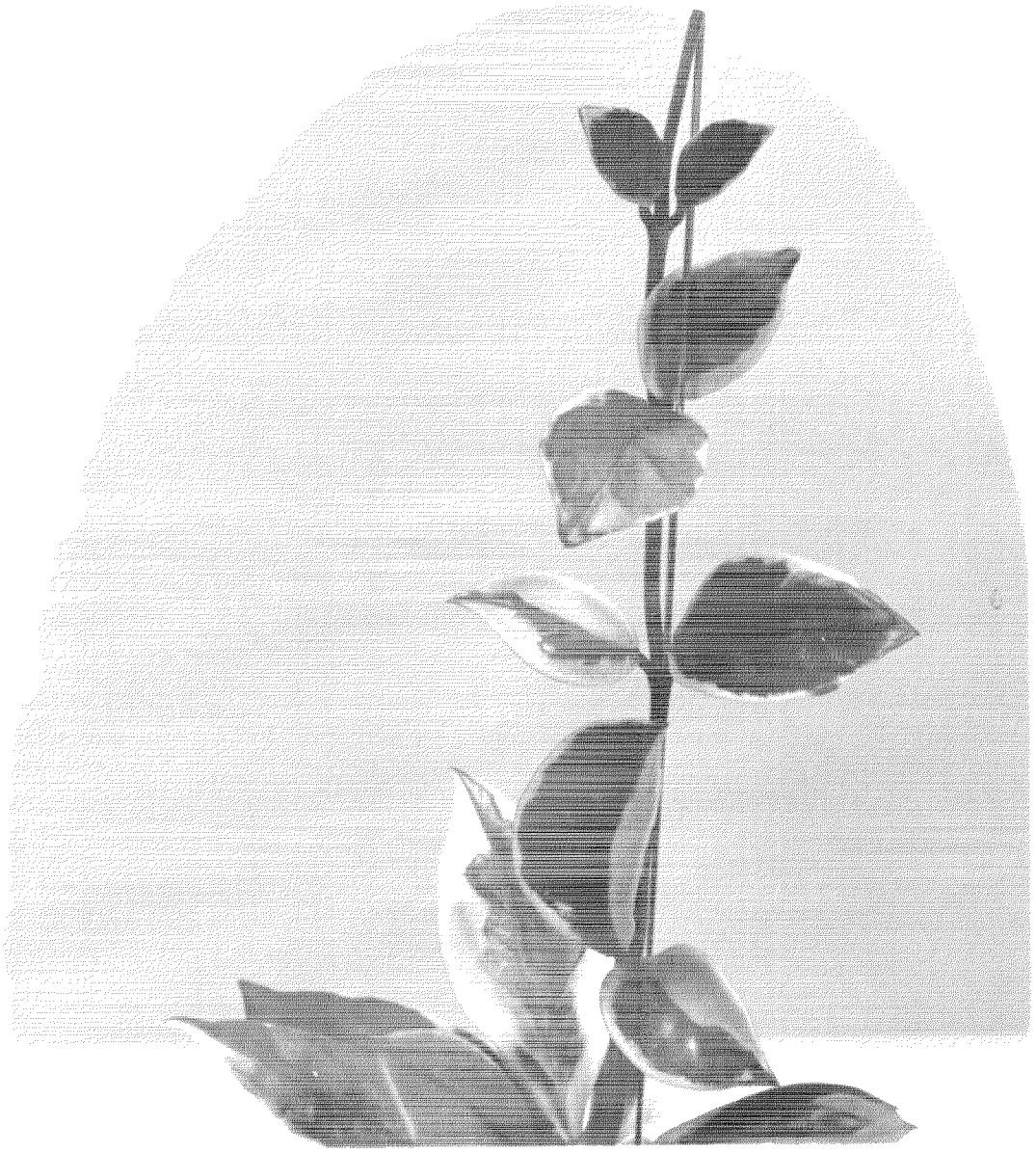
Figure 4:
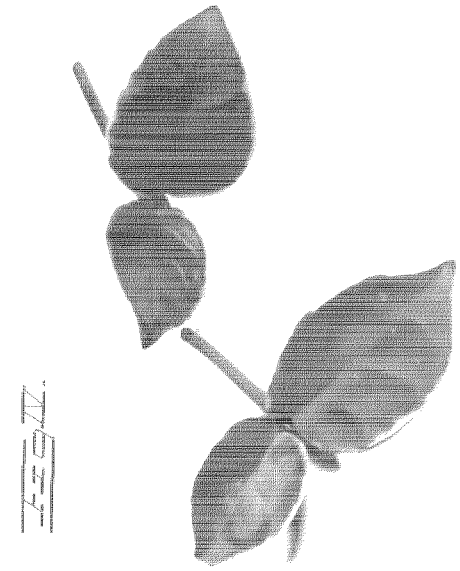
Figure 3:
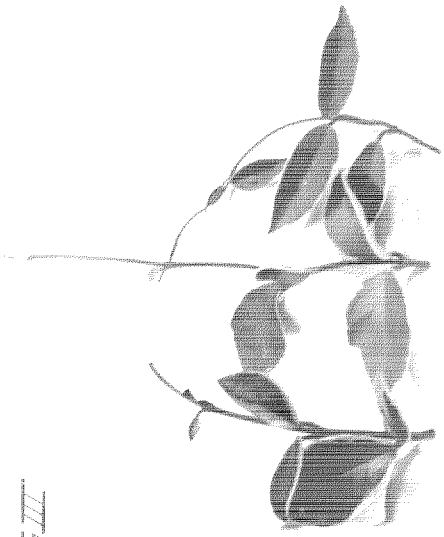
Figure 2:
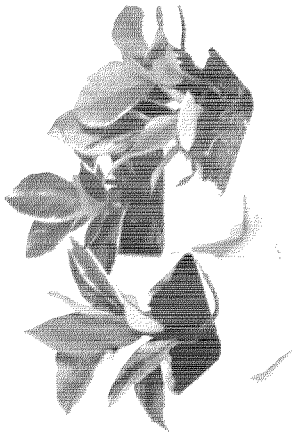
Figure 1:
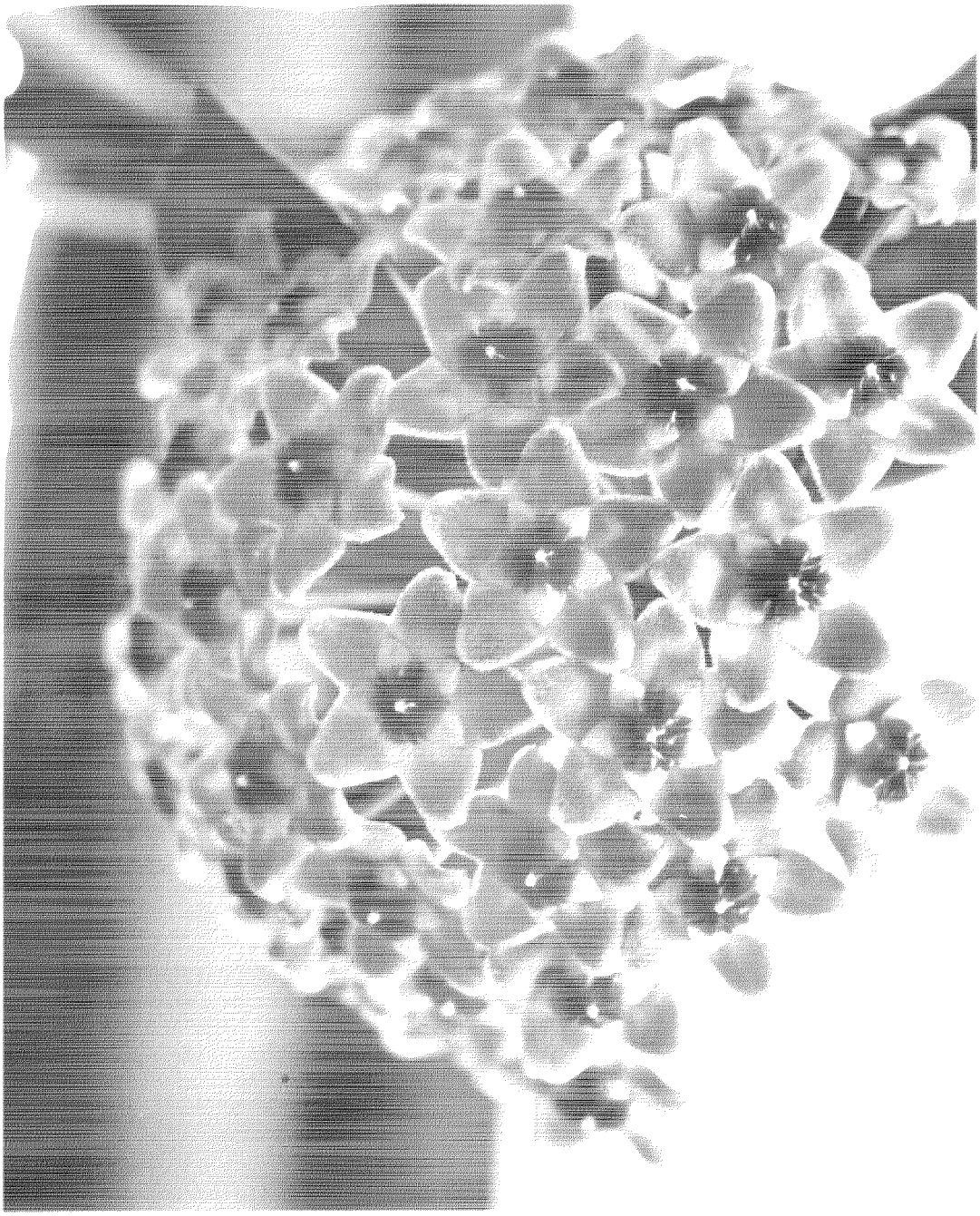

In patterns of leaf variegation, the new plants are comparable to both the unnamed and *Hoya carnosa variegata* varieties. However, plants of the new variety have a healthier and more robust appearance when compared to plants of the *Hoya carnosa variegata* variety, and in size and shape, the various plant parts closely compare to those of the unnamed variety. Apart from these characteristics, the new variety is distinguished from its antecendents and known related varieties in the following respects: (a) by stems, petioles, and peduncles which are characterized by dull, relatively long-lasting red to red-purple hues and which generally appear darker in comparison to the corresponding parts in plants of the unnamed and *Hoya carnosa variegata* varieties, (b) leaf blades which are characterized by variegated areas with attractive red and pink colors that gradually fade from the areas, (c) by leaf blades which are characterized by green fields that are overcast with red to red-purple hues which endow the fields with a blackish or sometimes brownish appearance to the ordinary eye and which gradually fade from the fields, (d) by an inflorescence with attractive purplish-red-colored pedicels, petals that have an attractive purplish-pink-colored upper epidermis and a purplish-red-colored lower epidermis, sepals with red-purple hues, and corona segments that are more corpulent in comparison to those of the *Hoya carnosa variegata* variety.

The invention relates to a new and distinct plant variety of the milkweed (Asclepiadaceae) family.

Certain plants of the milkweed family are well known in the foliage plant market and among these is the *Hoya carnosa variegata* variety. The leaf blades of this variety have a variegated or "albino" area that lacks chlorophyll and which is principally concentrated along the borders of the blades to surround a cetered field of green. In growth habit, plants of this variety have a tendency to produce larger area of variegation in leaves that develop at the first three nodes which appear on new stems and branches, and this frequently results in the appearance of entirely or nearly-entire albino leaves on new breaks that develop from the propagation of stem cuttings. The lack of chlorophyll frequently causes weaknesses in the variegated areas that result in deformed leaves, but the purchasing public has a preference for plants that have variegated leaves and consequently plants of the *Hoya carnosa variegata* variety have become popular items in the foliage plant market.

Several years ago, the inventor introduced to the market, a new plant variety that he developed by the propagation of stem cuttings taken from a mutation that was discovered on a plant of the *Hoya carnosa variegata* variety. This new variety was generally received in the foliage plant market as an improved strain of the *Hoya carnosa variegata* variety and remains unnamed. Plants of the unnamed variety resemble plants of the *Hoya carnosa variegata* variety and generally have the same color characteristics and patterns of leaf variegation that are found in the parent variety and, like the parent, also have the tendency to produce more highly variegated blade areas at the first three nodes on new breaks. The flowers of the unnamed variety are slightly larger than those of the *Hoya carnosa variegata* variety however, and apart from this characteristic, plants of the unnamed variety generally have a healthier, more robust appearance which is generally attributed to the fact that the stems, petioles and peduncles of the unnamed variety are characteristically slightly larger in diameter when compared to those of its antecedent, and that the leaf blades of the unnamed variety are characteristically slightly larger and rounder than the antecedent.

The variegated leaf blade areas in both varieties are usually yellowish white, pale yellow or thereabouts in color, and both varieties have a tendency to produce a variegated blade area in an occasional immature leaf which is light pink or thereabouts in color. This light pink color rapidly fades out of the variegated area and it is extremely rare that any of the color can be detected when the leaf reaches maturity.

The main object of the invention has been to develop a plant variety which is related in general appearance to plants of the *Hoya carnosa variegata* variety but which is distinguished by attractive red and pink colors in the variegated leaf blade areas and which appear in successive propagations as a true genetic variation. Yet another object has been to develop a plant variety which fulfills the main objective and additionally has the healthier and more robust appearance that is associated with the unnamed plant variety.

The objects of the invention have been fully realized as will be evident from the following detailed disclosure.

Plants of the new variety generally resemble and are related to both the unnamed and *Hoya carnosa variegata* varieties and are mainly distinguished from its antecedents and related varieties known to the inventor by certain color characteristics. The original plant of the new variety was discovered in a bed of plants which were being propagated from cuttings taken from plants of the unnamed variety and which were under cultivation in a nursery at Winter Garden, Fla. Since the initial discovery of the original plant, the plant has been asexually reproduced at Winter Garden, Fla., by the propagation, at the nursery of stem cuttings taken from the original plant.

Through successive propagations, it has been ascertained that plants of the new variety have parts which in size and shape closely compare to the corresponding plant parts of the unnamed variety, and that in patterns of leaf variegation, the new plants are comparable to both the unnamed and the *Hoya Carnosa variegata* varieties. It has also been ascertained that the tendency to produce more highly variegated leaves at the first three nodes on new breaks has been passed on to the descendant. Plants of the new variety thus generally resemble and are related to both the *Hoya carnosa variegata* and unnamed varieties but are distinguished from these antecedents and related varieties known to the inventor in the following respects: (1) by stems, petioles and peduncles which are characteristically slightly larger in diameter as compared to plants of the *Hoya carnosa variegata* variety and which are further characterized by dull, relatively long lasting, red to red-purple hues that provide a generally darker appearance in the plant parts as compared to the corresponding parts in plants of the unnamed and *Hoya carnosa varieaga* varieties, (2) by leaf blades which are characteristically slightly larger and rounder as compared to plants of the *Hoya carnosa variegata* variety and which are further characterized by variegated areas with attractive red and pink colors that gradually fade from the areas and green fields that are overcast with red to red-purple hues which endow the fields with a blackish or sometimes brownish appearance to the ordinary eye and thereafter gradually fade from the fields, and (3) by an inflorescence which is characterized by attractive purplish-red colored pedicels, petals that have an attractive purplish-pink colored upper epidermis and a purplish-red colored lower epidermis, sepals with red-purple hues, and corona segments that are more corpulent in comparison to those of the *Hoya carnosa variegata* variety.

The accompanying sheets of drawings serve, by color photographic means, to illustrate and also compare the new variety with certain of its antecedents and wherein:

FIG. I shows one plant of the new variety and illustrates colors found in the variegated areas of typical young mature leaves as well as in the older leaves of the new variety;

FIG. II shows three separate potted plants of the new variety with both young mature and older leaves appearing in the figure, and further illustrates some of the entirely or nearly-entire albino leaves that frequently develop at the first three nodes on new branches or breaks;

FIG. III shows tip end stem cuttings of comparable age taken, as appear from left to right in the figure, from plants of the new variety, the unnamed variety and the *Hoya carnosa variegata* variety;

FIG. IV shows stem cuttings with leaves of comparable age taken, as seen from left to right in the figure, from winter grown plants of the unnamed and new varieties, and serves to illustrate the overcast that appears in the green fields of the new variety;

FIG. V is an enlarged view of a node and an attached petiole of the new variety;

FIG. VI shows a peduncle and petiole of the new variety with a portion of the lower epidermis of an attached leaf blade;

FIG. VII shows an inflorescence of the new variety;

FIG. VIII shows a flower of the new variety at the left in the figure and another flower of the *Hoya carnosa variegata* variety at the right in the figure, and illustrates the slightly larger size of the flower and the fuller or more corpulent characteristic of the corona segments of the new variety;

FIG. IX shows the undersides of several flowers in an inflorescence of the new variety and serves to illustrate the calyx and lower epidermis of the flower petals; and FIG. X is another view of an inflorescence of the new variety and illustrates the colors of the pedicels as well as those of the stems, peduncles and immature petiole.

The following is a detailed description of the new plant variety with colors named where indicated in accord with the ISCC–NBS method of designating colors (U.S. Department of Commerce, National Bureau of Standards, Circular 553, issued Nov. 1, 1955) as interpreted from color notations derived by comparison with the current "Neighboring Hues Edition" of the Munsell Book of Color published by the Munsell Color Company, Inc., of Baltimore, Maryland.

PLANT DESCRIPTION

Parentage: Mutation of an unnamed variety that originated as a mutation of *Hoya carnosa variegata* plant.

Classification:

(A) *Botanic.*—*Hoya carnosa* (CV) (Asclepiadaceae) milkweed family.

(B) *Commercial.*—Foliage plant.

Form: Semisucculent, tropical, twining vine type perennial evergreen with some branching.

Stems:

(A) *General.*—Caulescent, fleshy, herbaceous.

(B) *Texture.*—Moderately pubescent during immaturity and with age becoming glabrous and ultimately covered with thick waxy scale.

(C) *Size.*—(1) Diameter—slightly larger than those of the *Hoya carnosa variegata* variety and usually 3/32"–3/16" at maturity. (2) Internode—usually less than 4" during first years growth of new break or branch with subsequent growth of break or branch being commonly 4"–6" between nodes.

(D) *Color.*—Dull, relatively long lasting red to red-purple hues which are gradually obscured by scale formations like those encountered in unnamed and *Hoya carnosa variegata* varieties. Commonly grayish-reddish-brown (ISCC–NBS) (7.5R 3/2), dark purplish-red (ISCC–NBS) (10RP 3/6), dark red (ISCC–NBS) (5R 3/4), dark grayish-red (ISCC–NBS) (2.5R 3/2), and dark grayish-reddish-brown (ISCC–NBS) (7.5R 2/2) (10R 2/1).

Leaves:

(A) *General.*—Simple, exstipulate leaf with a blade that is characterized by a variegated border area which surrounds a green field in patterns comparable to those found in unnamed and *Hoya carnosa variegata* varieties.

(B) *Arrangement.*—Opposite.

(C) *Margins.*—Usually entire with frequent, non-repeating, occurrences of undulate and other variant shapes.

(D) *Venation.*—Pinnate.

(E) *Shape.*—(1) General—usually elliptic with frequent, non-repeating occurrences of ovate, obovate, and other variant shapes. (2) Leaf apices—usually acute with frequent, non-repeating occurrences of acuminate, cuspidate and other variant shapes. (3) Leaf bases—usually acute with frequent, non-repeating occurrences of attenuate, obtuse, and other variant shapes.

(F) *Petioles.*—(1) General—fleshy. (2) Texture—slightly pubescent and with age becoming glabrous and ultimately covered with moderately thick waxy scale. (3) Size: (a) Diameter—slightly larger than those of the *Hoya carnosa variegata* variety and usually 3/32"–1/8" at maturity. (b) Length—usually 3/8"–1 1/4" at maturity. (4) Color—dull, relatively long lasting red to red-purple hues which are gradually obscured by scale formations like those encountered in unnamed and *Hoya carnosa variegata* varieties. Commonly dark purplish-red (ISCC–NBS) (7.5RP 3/4), dark red (ISCC–NBS) (2.5R 3/4), grayish-red (ISCC–NBS) (2.5R 4/4) and grayish-purple-red (ISCC–NBS) (10RP 5/6).

(G) *Leaf blades.*—(1) General—semisucculent. (2) Texture: (a) Upper epidermis—slightly pubescent during immaturity and becoming glabrous with smooth waxy surface during maturity. (b) Lower epidermis—moderately pubescent and heavily glaucous. (3) Size: (a) Length—usually 1 3/4"–3" at maturity. (b) Width—usually 1"–2" at maturity. (4) Color: (a) Upper epidermis—(1) Variegated area—attractive red and pink colors that gradulaly fade from the areas as the blades age. Commonly moderate purplish-red (ISCC–NBS) (7.5RP 5/10), (10RP (4/10) (10RP 5/8), deep purplish-pink (ISCC–NBS) (7.5RP 6/10), and moderate purplish-pink (ISCC–NBS) (7.5RP 7/8) (10RP 4/10) in young mature blades (30–60 days old) which mature under "Florida Winter Nursery Conditions." Commonly moderate purplish-pink (ISCC–NBS) (7.5RP 7/8) (10RP 4/10), deep pink (ISCC–NBS) (10RP 6/8), strong pink (ISCC–NBS) (10RP 7/8) (2.5R 7/8), light-moderate yellowish-pink (ISCC–NBS) 7.5R 8/4), pale purplish-pink (ISCC–NBS) (7.5RP 8/4), and moderate pink (ISCC–NBS) (10RP 7/6) in young mature blades (30–60 days old) that mature under "Florida Summer Nursery Conditions." Commonly yellowish-white (ISCC–NBS) (7.5Y 9/2), pale greenish-yellow (ISCC–NBS) (7.5Y 9/4) (10Y 9/4), light greenish-yellow (ISCC–NBS) (7.5Y 9/5), pale yellow (ISCC–NBS) (5Y 9/4) and pale yellow green (ISCC–NBS) (10Y 9/2) after red and pink colors fade from the areas. (2) Green field—characteristically overcast with red to red-purple hues that are concentrated in the upper epidermal region of leaf blade and which, to the ordinary eye, endow the fields with a blackish or sometimes brownish appearance that gradually fades from the fields but which is longer lasting in blades that mature under "Florida Winter Nursery Conditions" than blades which mature under "Florida Summer Conditions." Commonly purplish-black, blackish-purple, dark grayish-purple (ISCC–NBS) (near 10RP 2/1) (near 7.5RP 2/1), reddish-black, blackish-red, dark grayish-red (ISCC–NBS) (near 2.5R 2/1) (near 5R 2/1), and dark grayish-reddish-brown (ISCC–NBS) (near 10R 2/1) in immature blades (7–15 days post embryonic) grown under "Florida Summer Nursery Conditions" and in young mature blades (30–60 days old) grown under "Florida Winter Nursery Conditions." Commonly yellow green (ISCC–NBS) (2.5GY 5/6) 5GY 5/6) (5GY 5/6) 7.5GY 5/6), strong yellow green (ISCC–NBS) (5GY 6/8) moderate olive green (ISCC–NBS) (7.5GY 4/4) (7.5GY 4/6), and moderate olive (ISCC–NBS) (5Y 4/4) after the overcast fades from the green fields. (b) Lower epidermis—same color characteristics as found in *Hoya carnosa variegata* and unnamed varieties.

Growth habit: Vigorous in tropical and semi-tropical environments with some branching. Tendency, like unnamed and *Hoya carnosa variegata* varieties, on new breaks or branches to produce larger areas of leaf variegation and with frequent entirely or nearly entire albino leaves at the first three nodes next adjacent the older stems. Lower temperatures and/or more shading during growth period tend to produce darker initial colors in the variegated areas and more intense purplish color components in the variegated and green fields areas of the blades.

Inflorescence form: Simple umbel with minute 5-merous bracts and usually 20–40 flowers in a cluster.

Peduncles:

(A) *General.*—Hard, fleshy.

(B) *Texture.*—Slightly pubescent and with age becoming glabrous and ultimately covered with thick waxy scale.

(C) *Size.*—(1) Length—usually ½"–1½". (2) Diameter—slightly larger than those of the *Hoya carnosa variegata* variety and usually 3/32"–5/32".

(D) *Color.*—Characteristically dull, relatively long lasting red to red-purple hues which are gradually obscured by scale formations like those encountered in unnamed and *Hoya carnosa variegata* varieties. Commonly moderate reddish-brown (ISCC–NBS) (7.5R 3/4), dark red (ISCC–NBS) (5R 3/4) (2.5R 3/4), and dark purplish-red (ISCC–NBS) (10RP 3/4).

Pedicels:

(A) *General.*—Soft, fleshy.

(B) *Texture.*—Sparcely pubescent.

(C) *Size.*—(1) Length—usually 1"–1½". (2) Diameter—usually 1/32"–3/32".

(D) *Color.*—Attractive purplish-red colored and commonly moderated purplish-red (ISCC–NBS) (10RP 4/10) (10RP 4/8) (7.5RP 4/8), and dark purplish-red (ISCC–NBS) (7.5RP 3/6).

Flowers:

(A) *General.*—Complete, perfect, actinomorphic and 5-merous type flower with hypogynous perianth and alternate sepal-petal and petal-corona segment arrangements.

(B) *Size.*—Comparable to unnamed variety and slightly larger than *Hoya carnosa variegata* variety.

(C) *Calyx.*—(1) General—5-merous with separate, valvate sepals. (2) Sepal texture: (a) Lower epidermis—moderately pubescent. (b) Upper epidermis—glabrous. (3) Sepal color—characterized by red-purple hues in lower epidermis which are commonly dark purplish-red (ISCC–NBS) (10RP 3/4) (10RP 3/6) and dark grayish-purple (ISCC–NBS) (7.5RP 3/2) (7.5RP 2/2).

(D) *Corolla.*—(1) General—5-merous, valvate and rotate with interpetal basal fusion for about ½ petal length. (2) Petal texture: (a) Upper epidermis—very dense, velvety pubescent. (b) Lower epidermis—glabrous and waxy. (3) Petal color: (a) Upper epidermis—attractive purplish-pink colors which are commonly dark purplish-pink (ISCC–NBS) (5RP 6/8) and moderate purplish-pink (ISCC–NBS) (5RP 7/6). (b) Lower epidermis—attractive purplish-red colors which are commonly dark purplish-red (ISCC–NBS) (7.5RP 3/6) (5RP 3/8), moderate purplish-red (ISCC–NBS) (7.5RP 4/8) (10RP 4/10) and grayish-purplish-red (ISCC–NBS) (5RP 4/6).

(E) *Corona.*—(1) General—5-merous horn-like segments which are adnate to stigma and corolla and crested at their proximal ends. Characteristically more corpulent than segments of *Hoya carnosa variegata* variety. (2) Segment texture—hard, smooth waxy and glabrous. (3) Segment color: (a) Proximal end—commonly dark purplish-red (ISCC–NBS) (7.5RP 3/6) (7.5RP 3/4) (5RP 3/4) and merging with distal end color with occasional color variations within flower and inflorescence. (b) Distal end—commonly yellowish-white (ISCC–NBS) (10Y 9/1) (5Y 9/1) and pale yellow green (ISCC–NBS) (10Y 9/2).

(F) *Androecium.*—(1) General—5-merous pollinium pairs partially enclosed by expanded translucent perenchymatous translators and attached to stigma through corpuscula located between adjacent segments and with pollinia and translators rising above corpuscula and stigma in converging conical arrangement. (2) Pollinium color—commonly vivid yellow (ISCC–NBS) (2.5Y 8/10) and brilliant yellow (ISCC–NBS) (2.5Y 8/10).

(G) *Gynoecium.*—(1) General—compound and apocarpous pistil with common stigma. (2) Stigma—5-lobed, waxy and near light brilliant yellow (ISCC–NBS) (5Y 9/8). (3) Style—lacking. (4) Ovary—two monocarpellate ovularies with axillary placentation of ovules.

The above description is based on observations of well fertilized plants grown under 85% shaded nursery conditions in the Winter Garden, Fla. area and wherein temperatures range approximately from 60 degrees to 85 degrees fahrenheit during the winter months and from 75 degrees to 95 degrees fahrenheit during the summer months.

The following is a description of a plant of the new variety which was grown under well fertilized and 85% shaded nursery conditions in central Florida with colors recorded in August and reported in accord with the Munsell Color system of notations (hue value/chroma).

Length of main step: Approximately 50 inches.

Number of nodes: 25 plus two with embryonic leaves.

Inflorescence location: 25th node from rooted stem cutting.

| | Node (From Rooted Stem) | | | |
|---|---|---|---|---|
| | 4 | 13 | 23 | 25 |
| Stem: | | | | |
| Dia.[1] (in.) | 7/32 | 7/32 | 7/32 | 3/16 |
| Color [1] | Scaled | Scaled | (7.5R 3/2) | (2.5R 3/2) |
| Left Leaves: | | | | |
| Blade Width (in.) | 1½ | 1 9/16 | 1¾ | 1½ |
| Blade Length (in.) | 2½ | 2 | 2⅛ | 1 15/16 |
| Petiole Dia. (in.) | ⅛ | ⅛ | ⅛ | 3/32 |
| Petiole Length (in.) | ⅝ | ½ | 7/16 | ⅜ |
| Petiole Color (in.) | (2.5R 4/4 | (2.5R 4/4) | (10RP 5/6) | (7.5RP 3/4) |
| Var. Area Color | (5Y 9/4) | (5Y 9/4) | (10RP 7/8) | (7.5RP 8/4) |
| Green Field Color | (5GY 5/6) | (5GY 6/8) | (5GY 6/8) | (2.5GY 5,6) |
| Right Leaves | 1 1/16 | 1 9/16 | 1½ | 1⅜ |
| Blade Length (in.) | 1⅞ | 2 1/16 | 2 | 1⅞ |
| Petiole Dia. (in.) | ⅛ | ⅛ | ⅛ | ⅛ |
| Petiole Length (in.) | ⅝ | 9/16 | ½ | 7/16 |
| Petiole Color | (10RP 5/6) | (2.5R 3/4) | (2.5R 3/4) | (7.5RP 3/4) |
| Var. Area Color | (10Y 9/4) | (7.5Y 9/4) | (10RP 7/6) | (7.5RP 7/8) |
| Green Field Color | (5GY 6/8) | (5GY 6/8) | (5GY 6/6) | (5Y 4/4) |

[1] Taken below node.

Peduncle: Length (in.), 1 5/16.
Diameter (in.), ⅛.
Color, (10RP 4/8).
Pedicels No. 32
Length (in.), 1 5/16 av.
Diameter (in.), Average about 1/16.
Color, (10RP 4/8).
Flowers: Sepal colors, (10RP 3/4).
Petal colors, Upper epidermis (7.5RP 7/6).
Lower epidermis (10RP 4/10).
Corona Segment Color, proximal ends: predominately (5RP 2/4), distal ends: predominately (5Y 9/1).

The following is a description of a plant of the new variety which was grown under well fertilized and 85% shaded nursery conditions in central Florida and with colors recorded in November and reported in accord with the Munsell Color system of notation (hue value/corona).

Length of main stem: Approximately 14 inches.
Number of nodes: 6 plus two with embryonic leaves.
Inflorescence location: Absent.

scribed, and which is principally distinguished (1) by stems, petioles and peduncles which are characteristically slightly larger in diameter as compared to those in plants of the *Hoya Carnosa Variegata* variety and which are further characterized by dull, relatively longlasting, red to red-purple hues that provide a generally darker appearance in the plant parts as compared to the corresponding parts in plants of the *Hoya Carnosa Variegata* variety. (2) by leaf blades which are characteristically slightly larger and rounder as compared to those in plants of the *Hoya Carnosa Variegata* variety and which are further characterized by variegated areas with attractive red and pink colors that gradually fade from the areas, and by green fields that are overcast with red to red-purple hues which endow the fields with a blackish or sometimes brownish appearance to the ordinary eye and thereafter gradually fade from the fields, and (3) by an inflorescence which is characterized by attractive purplish-red colored pedicels, petals that have an attractive purplish pink colored upper epidermis and a purplish-red colored lower epidermis, sepals with red-purple hues, and corona seg-

| Node (from Rooted Cutting) | Rooted Stem. | 1 | 2 | 3 | 4 | 5 | 6 |
|---|---|---|---|---|---|---|---|
| Post embryonic leaf age (approx.) | 6–8 mos. | 90 days | 60 days | 30 days | 20 days | 15 days | 7 days |
| Stem color [3] | | | 2.5R 3/2 | 7.5R 3/2 | 7.5R 2/2 | 10R 2/1 | 10R 2/1 |
| Blade length (in.): | | | | | | | |
| Left | 2⅝ | 2⅞ | 2¼ | 2¼ | 1⅝ | 1½ | 9/16 |
| Right | 2¼ | 3 | 2⅝ | 1⅞ | missing | 1½ | ½ |
| Blade width (in.): | | | | | | | |
| Left | 1¾ | 1½ | 1⅜ | 1⅝ | ⅞ | ¾ | 5/16 |
| Right | 1⅝ | 1½ | 1¾ | 1½ | missing | ¾ | ¼ |
| Petiole dia.: | | | | | | | |
| Left | ⅛ | ⅛ | ⅛ | 3/32 | 3/32 | 3/32 | 1/16 |
| Right | ⅛ | ⅛ | ⅛ | 3/32 | missing | 3/32 | 1/16 |
| Petiole color: | | | | | | | |
| Left | 2.7y 5/4 | 2.7y 4/4 | 7.5y 6/4 | 10RP 3/2 | 7.5RP 3/2 | 7.5RP 3/4 | 7.5RP 3/2 |
| Right | 2.5y 5/4 | 2.5y 4/4 | 7.5y 6/4 | 10RP 3/2 | missing | 7.5RP ¾ | 7.5RP 3/2 |
| Variegated area color: | | | | | | | |
| Left | Near 10y 9/2 | 7.5y 9/4 | 7.5y 9/2 | 10RP 7/6 | 10RP 5/8 | 10RP 4/10 | 10RP 4/8 |
| Right | Near 10y 9/2 | 7.5y 9/2 | 7.7y 9/2 | 10RP 6/8 | missing | 10RP 4/10 | 10RP 4/8 |
| Green field color: | | | | | | | |
| Left | 7.5Gy 4/6 | 7.5Gy 4/6 | 7.5Gy 4/4 | Near 7.5Gy 3/4 [1] | Near 5Gy 3/1 | Near 10RP 2/2 | Near 10RP 2/1 |
| Right | 7.5Gy 4/6 | 7.5Gy 4/6 | 7.5Gy 4/4 | Near 7.5Gy 3/4 [1] | missing | Near 10RP 2/1 | Near 17.5R 2/1 |

[1] With very slight reddish overcast.
[2] With slight reddish overcast.
[3] Taken below mode.

I claim:

1. The new and distinct plant variety *Hoya Carnasa* of the milkweed family which is related to and generally resembles the *Hoya Carnosa Variegata* variety in patterns of leaf variegation, substantially as herein shown and dements that are more corpulent in comparison to those of the *Hoya Carnosa Variegata* variety.

No references cited.

ROBERT E. BAGWILL, Primary Examiner

PO-1050
(5/69)

UNITED STATES PATENT OFFICE
CERTIFICATE OF CORRECTION

Plant

Patent No. 2950 Dated December 9, 1969

Inventor(s) Barnell L. Cobia

It is certified that error appears in the above-identified patent and that said Letters Patent are hereby corrected as shown below:

Column 1, Line 58, "cetered" should be -- center --;
Line 60, "area" should be -- areas --;
Column 5, Line 32, "(5 GY 5/6)" (second occurrence) should be -- (5 GY 6/6) --;

In the tabulated information at the top of Column 7, the following line should be inserted under the line commencing with "Right Leaves"
-- Blade Width (in.) 1 1/16 1 9/16 1 1/2 1 3/8 --;

In the tabulated information at the bottom of Columns 7 and 8, in the column headed "Rooted Stem", "2.7 Y 5/4" should be -- 2.5 Y 5/4 --;
in the column headed "1", "2.7 Y 4/4" should be -- 2.5 Y 4/4 --;
in the column headed "2", "7.7 Y 9/2" should be -- 7.5 Y 9/2 --;
in the column headed "4", "near 5 GY 3/1" should be -- near 5 GY $3/1^2$ --.

SIGNED AND
SEALED
JUN 23 1970

(SEAL)
Attest:

Edward M. Fletcher, Jr.
Attesting Officer

WILLIAM E. SCHUYLER, JR.
Commissioner of Patents